United States Patent [19]

Suh et al.

[11] Patent Number: 4,507,312
[45] Date of Patent: Mar. 26, 1985

[54] ANTIHYPERTENSIVE AMIDES

[75] Inventors: John T. Suh, Greenwich, Conn.; Jerry W. Skiles, Tuckahoe, N.Y.; Bruce E. Williams, Cottage Grove, Minn.; Alfred Schwab, Williston Park, N.Y.

[73] Assignee: USV Pharmaceutical Corporation, Tarrytown, N.Y.

[21] Appl. No.: 323,852

[22] Filed: Nov. 23, 1981

Related U.S. Application Data

[60] Division of Ser. No. 200,180, Oct. 24, 1980, Pat. No. 4,304,771, Continuation-in-part of Ser. No. 57,175, Jul. 13, 1979, Pat. No. 4,256,761.

[51] Int. Cl.³ ............... A61K 31/34; C07D 307/06
[52] U.S. Cl. ................... 514/471; 549/480; 514/472
[58] Field of Search .............. 549/480; 424/285

[56]  References Cited
U.S. PATENT DOCUMENTS 4,256,761  3/1981  Suh et al. .................. 549/480

Primary Examiner—Henry R. Jiles
Assistant Examiner—Robert C. Whittenbaugh

[57]  ABSTRACT

Compounds of the structure:

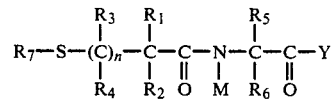

wherein $R_1$, $R_2$, $R_3$, $R_4$, $R_5$, and $R_6$ are hydrogen, alkyl, alkenyl, alkynyl, phenyl-alkyl, or cycloalkyl, n is an integer from 0 to 4 inclusive, M is heterocyclic or heterocyclic alkyl, Y is hydroxy, alkoxy, amino, or substituted amino, amino-alkanoyl, aryloxy, aminoalkoxy, or hydroxyalkoxy, and $R_7$ is hydrogen, alkanoyl, carboxylalkanoyl, hydroxyalkanoyl, amino-alkanoyl, cyano, amidino, carbalkoxy, ZS, or

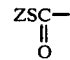

wherein Z is hydrogen, alkyl, hydroxyalkyl, aminoalkyl or the radical

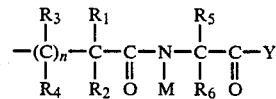

wherein $R_1$, $R_2$, $R_3$, $R_4$, $R_5$, $R_6$, n, M and Y are as described above; and where Y is hydroxy their nontoxic, pharmaceutically acceptable alkali metal, alkaline earth metal, and amine salts.

11 Claims, No Drawings

ANTIHYPERTENSIVE AMIDES

This application is a division of application Ser. No. 200,180, filed Oct. 24, 1980, now U.S. Pat. No. 4,304,771, issued Dec. 8, 1981, which was a continuation-in-part of application Ser. No. 57,175, filed July 13, 1979, now U.S. Pat. No. 4,256,761, issued Mar. 17, 1981.

This invention relates to new chemical compounds having valuable pharmaceutical activity. It particularly relates to amides having antihypertensive and angiotensin converting enzyme inhibitory activity and of the structure

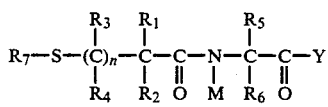

wherein
$R_1$, $R_2$, $R_3$, $R_4$, $R_5$, and $R_6$ are hydrogen, alkyl, alkenyl, alkynyl, phenyl-alkyl, and cycloalkyl, and may be the same or different,
n is an integer from 0 to 4 inclusive,
M is heterocyclic or heterocyclic alkyl,
Y is hydroxy, alkoxy, amino, or substituted amino, amino-alkanoyl, aryloxy, aminoalkoxy, or hydroxyalkoxy, and
$R_7$ is hydrogen, alkanoyl, carboxyalkanoyl, hydroxyalkanoyl, aminoalkanoyl, cyano, amidino, carbalkoxy, ZS, or

wherein Z is hydrogen, alkyl, hydroxyalkyl, or the radical

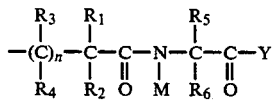

wherein $R_1$, $R_2$, $R_3$, $R_4$, $R_5$, $R_6$, n, M and Y are as described above; and where Y is hydroxy, their nontoxic, pharmaceutically acceptable alkali metal, alkaline earth metal, and amine salts.

The alkyl groups per se and in the alkyl moiety in aralkyl, cycloalkyl-alkyl, polycycloalkyl-alkyl, heteroaryl-alkyl and the like, and, in alkoxy, alkylthio, alkanoyl, carbalkoxy, and alkylamino, may be straight-chained or branched and are preferably lower alkyl groups containing from 1 to 6 carbons. Such groups include methyl, ethyl, propyl, isopropyl, butyl, isobutyl, amyl, iso-amyl, hexyl, and the like.

The alkenyl and alkynyl groups may also be branched or straight-chained and contain from 2 to 6 carbon atoms. Such groups include vinyl, ethynyl, propenyl, allyl, isopropenyl, and the like.

The cycloalkyl groups may be mono or polycyclic and contain from 3 to 16 carbon atoms. The M heterocyclic groups may be mono or polycyclic and include such groups as pyridyl, quinolyl, piperidyl, pyrrolyl, morpholinyl, thiomorpholinyl, furyl, furfuryl, tetrahydrofurfuryl, thienyl, tetrahydrothienyl, imidazolyl, benzimidazolyl, and the like. These groups may carry substituents such as alkyl, alkenyl, alkynyl, hydroxy, thio, amino, alkylamino, dialkylamino, alkoxy, alkylthio, and halo. The sulfur in the tetrahydrothienyl may be oxidized to the sulfone.

The preferred compounds are those wherein $R_1$, $R_3$, $R_4$, $R_5$ and $R_6$ are hydrogen, $R_2$ is lower alkyl, preferably methyl, $R_7$ is hydrogen or lower alkanoyl, n is 1, Y is hydroxy, and M is thienyl, tetrahydrothienyl, and tetrahydrothienyl-sulfone.

The compounds of the present invention are prepared by the reaction of an appropriately substituted amino acid ester of the structure

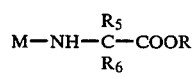

with a carboxylic acid of the structure

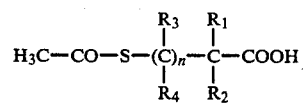

followed by the stepwise hydrolysis of (i) the ester to yield the free carboxylic acid and (ii) the acetyl group to yield the free thiol, providing a compound of the structure

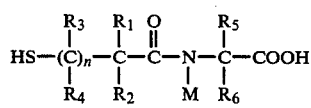

In these formulae, R is lower alkyl, preferably t-butyl and $R_1$, $R_2$, $R_3$, $R_4$, $R_5$, $R_6$, M and n are as defined above.

It is known to those skilled in the art that those amides of the present invention having an asymmetric carbon atom may exist in racemic or optionally active levo or dextro forms. All of these forms are contemplated within the scope of this invention.

The invention will be more fully illustrated in the examples which follow. These examples are given by way of illustration and are not to be considered as limiting.

EXAMPLE 1 t-Butyl bromoacetate

Bromoacetic acid (484 g, 3.48 mol) was dissolved in methylene chloride (1000 ml) and concentrated sulfuric acid (5 ml) was added as catalyst. The resulting solution was cooled in a dry-ice acetone bath and isobutylene was bubbled through the solution for an hour and a half. The flask was lightly stopped with a gas venting stopper and allowed to stand at room temperature overnight. Aqueous potassium carbonate (10%) was added and the layers were separated. The aqueous layer was discarded and the organic layer was washed once more with aqueous potassium carbonate (10%), once with water, dried over magnesium sulfate, and filtered. Evaporation of the solvent afforded t-butyl bromoacetate as a pale yellow oil (600 g, 88.4%).

EXAMPLE 2

2-Acetylthio-1-methylpropionic acid

Thiolacetic acid (1000 g, 13.2 mol) was placed in a five-liter round bottom flask and cooled in an ice bath. Methacrylic acid (610 g, 7.09 mol) was added with vigorous stirring. Cooling was continued for fifteen minutes and then the reaction mixture was heated to a gentle reflux for one hour. Stirring was continued at room temperature for six days. Excess thiolacetic acid was removed in vacuo and the residue was dissolved in chloroform. The chloroform was washed four times with water and dried over magnesium sulfate. Filtration and evaporation of the solvent yielded a yellowish-orange oil which was vacuum distilled at 100° C. to give the product initially as a yellow oil which slowly crystallized. Addition of ether and filtration of the product afforded a pale yellow solid (890 g, 77.5%), m.p. 35°–37°.

EXAMPLE 3

2-Acetylthio-1-methylpropionyl chloride

2-Acetylthio-1-methylpropionic acid (6.3 g, 0.0389 mol) was dissolved in toluene (50 ml) and five drops of pyridine was added. Thionyl chloride (10 ml) was added in one portion and the resulting mixture was stirred at room temperature for one and a half hours. The toluene was evaporated on a rotary evaporator and water was added to the residue. The product was extracted three times with chloroform. The combined chloroform extract was washed twice with 5% sodium bicarbonate and twice with water. The chloroform was dried over magnesium sulfate, filtered and evaporated to afford (6.9 g, 98.3%) of the product as a pale yellow oil.

EXAMPLE 4

N-(3-Acetylthio-2-methylpropanoyl)-N-tetrahydrofurfurylglycine tert-butyl ester To a solution of N-tetrahydrofurfurylglycine tert-butyl ester (6.6 g, 0.0307 mol) and 3-acetylthio-2-methylpropionic acid (5.3 g, 0.0307 mol) in dry methylene chloride (150 ml) chilled in an ice bath was added dicyclohexylcarbodiimide (6.7 g, 0.0325 mol). The resulting mixture was stirred with cooling for 30 minutes and then overnight at room temperature. Precipitated dicyclohexylurea was filtered and washed with a small amount of methylene chloride. Concentration of the filtrate afforded crude product as a thick yellow oil which was used without further purification.

EXAMPLE 5

N-(3-mercapto-2-methylpropanoyl)-N-tetrahydrofurfurylglycine

Anhydrous ammonia was bubbled for fifteen minutes through methanol (150 ml) and the resulting ammonia saturated solution was added in one portion to N-(3-acetylthio-2-methylpropanoyl)-N-tetrahydrofurfurylglycine (7 g, 0.0231 mol) and the system was placed under a slight pressure of nitrogen. The resulting solution was stirred at room temperature for two hours. The solvent was removed in vacuo and the residue was applied to a column of AG-50W-X2 (Bio-Rad Laboratories) cation exchange resin and eluted with methanol. Methanol was evaporated and the residue was dissolved in chloroform. The chloroform was washed once with water and dried over magnesium sulfate. Filtration and evaporation of the solvent afforded a yellowish-orange oil which was purified by HPLC using the following solvent system: ethyl acetate/n-hexane/acetic acid (40:60:1). In this manner pure product was obtained as a colorless oil (3.9 g, 64%). The product was characterized as its DCHA salt, recrystallized from isopropanol, m.p. 128°–130° C.

EXAMPLE 6

N-(3-Pyridylmethylene)glycine ethyl ester

Glycine ethyl ester hydrochloride (42.1 g, 0.302 mole) were dissolved in methanol (500 ml) in a one-liter round bottom flask which contained a stirring bar and a nitrogen inlet. Concentrated hydrochloric acid was added dropwise to pH 0 and the resulting solution was stirred at room temperature for 30 minutes. Sodium cyanoborohydride (15 g, 0.239 mole) was then added portionwise over 30 minutes. The resulting mixture was stirred for 2½ hours at room temperature while periodically checking the pH of the mixture. The pH was kept at 0 to 3 by the dropwise addition of hydrochloric acid. Most of the methanol was evaporated to give a yellow pasty residue. Water was added to the residue and the mixture was basified to pH 8–9 with concentrated ammonium hydroxide. The product was extracted several times into chloroform and the combined chloroform extracts were washed with water and dried over magnesium sulfate. Filtration and evaporation of the solvent afforded the crude product as a yellow liquid (35 g). The product was further purified by HPLC using a step gradient procedure. Nonpolar material was eluted using ethyl acetate/ammonium hydroxide (98:2) as eluent. The polar product was eluted using the solvent system of acetonitrile/methanol/ammonium hydroxide (90:8:2) to give pure product as a yellow oil (28 g, 48%).

EXAMPLE 7

N-(3-Acetylthio-2-methylpropanoyl)-N-(3'-pyridylmethyleneglycine)ethyl ester To a solution of N-(3-pyridylmethylene)glycine ethyl ester (6.2 g, 0.032 mol) and 3-acetylthio-2-methylpropionic acid (5.2 g, 0.032 mol) in methylene chloride (100 ml) was added dicyclohexylcarbodiimide (6.8 g, 0.0330 mol). Stirring was continued at room temperature overnight. Precipitated dicyclohexylurea was filtered and washed with a small amount of cold diethyl ether. Evaporation of the filtrate afforded the crude product as an orange oil (12.5 g). The product was purified by HPLC using a step gradient procedure. Nonpolar material was eluted using ethyl acetate/ammonium hydroxide (98:2) as eluent. The polar product was eluted using the solvent system of acetonitrile/methanol/ammonium hydroxide (90:8:2) to give the pure product as a pale yellow oil (8.4 g, 80%).

EXAMPLE 8

N-(3-Acetylthio-2-methylpropanoyl)-N-(2'-methylene-1'-ethylpyrrolidine)glycine tert-butyl ester To a solution of N-(2'-methylene-1'-ethylpyrrolidine)glycine tert-butyl ester (10.2 g, 0.042 mol) and 3-acetylthio-2-methylpropionic acid (6.8 g, 0.042 mol) in dry methylene chloride (200 ml) chilled in an ice bath was added dicyclohexylcarbodiimide (8.7 g, 0.042 mol). The resulting mixture was stirred overnight at room temperature. Precipitated dicyclohexylurea was filtered and washed with a small amount of methylene chloride.

Concentration of the filtrate afforded product as a dark auburn oil (18.1 g).

EXAMPLE 9

N-(3-Mercapto-2-methylpropanoyl)-N-(2'-methylene-1'-ethylpyrrolidine)glycine Crude N-(3-acetylthio-2-methylpropanoyl)-n-(2'-methylene-1'-ethylpyrrolidine)glycine tert-butyl ester (10.0 g, 0.026 mol) was dissolved in a mixture of anisole (20 ml) and trifluoroacetic acid (60 ml). The resulting solution was stirred at room temperature for two hours. Trifluoroacetic acid was evaporated in vacuo and the residue was distributed between ethyl acetate and saturated aqueous sodium bicarbonate. The aqueous bicarbonate phase was separated and washed twice with ethyl acetate. The aqueous bicarbonate phase was then saturated with ammonium chloride and placed in a heavier than water continuous liquid extractor. The product was continuously extracted into chloroform over 16 hours. The chloroform was dried over magnesium sulfate, filtered and evaporated to give the mercaptan as an oil (4.3 g, 57%). The product was characterized as its DCHA salt which was prepared in ether to give colorless crystals, m.p. 120°–122° C.

EXAMPLE 10

N-(3-Acetylthio-2-methylpropanoyl)-N-furfurylglycine

Crude N-(3-acetylthio-2-methylpropanoyl)-N-furfurylglycine tert-butyl ester (14.6 g, 0.0407 mol) was dissolved in a mixture of anisole (20 ml) and trifluoroacetic acid (65 ml). The resulting solution was stirred at room temperature for two hours. The solvent was evaporated in vacuo and the residue was distributed between ethyl acetate and saturated aqueous sodium bicarbonate. The aqueous bicarbonate extract was washed twice with ethyl acetate and then acidified cautiously with concentrated hydrochloric acid to pH 4–5. The product was extracted several times into chloroform and the chloroform was washed twice with water. The organic phase was dried over magnesium sulfate, filtered and evaporated to give crude product as a pale yellow oil which was purified by HPLC using the following solvent system: ethyl acetate/n-hexane/acetic acid (40:60:1) to give pure product as a colorless oil (5.5 g, 44.7%). The product was purified by its DCHA salt which was prepared in ether, m.p. 140°–141° C.

EXAMPLE 11

N-(3-Mercapto-2-methylpropanoyl)-N-furfurylglycine

Anhydrous ammonia was bubbled for ten minutes through methanol (200 ml) and the resulting ammonia saturated solution was added in one portion to N-(3-acetylthio-2-methylpropanoyl)-N-furfurylglycine (8 g, 0.0264 mol) and the resulting colorless solution was placed under nitrogen. The resulting solution was stirred at room temperature for one and a half hours. The solvent was removed in vacuo and the residue was applied to a column of AG-50W-X2 (Bio-Rad Laboratories) cation exchange resin and eluted with methanol. Methanol was evaporated and the residue was dissolved in chloroform. The chloroform was washed once with water and dried over magnesium sulfate. Filtration and evaporation of the solvent afforded crude product as an oil which was purified by HPLC using the following solvent system: ethyl acetate/n-hexane/acetic acid (35:60:1), to give pure colorless oil (5.4 g, 80%). The product was characterized as its DCHA salt, m.p. 150°–153° C.

By following the procedures described in the above examples, the following additional compounds were prepared:

N-(3-Mercapto-2-methylpropanoyl)-N-(furyl)glycine

N-(3-Mercapto-2-methylpropanoyl)-N-(5-benzofuryl)glycine

N-(3-Mercapto-2-methylpropanoyl)-N-(furfuryl)glycine

N-(3-Mercapto-2,2-dimethylpropanoyl)-N-(3-thienyl)glycine

N-(3-Benzoylthio-2-methylpropanoyl)-N-(3-thiazolyl)glycine

N-(3-Mercapto-3-methylbutanoyl)-N-(2-benzothienyl)glycine

N-(2-Mercapto-2-methylpropanoyl)-N-(4-tetrahydrothiopyranyl)glycine

N-(3-Mercapto-2-methylpropanoyl)-N-1-(2-thienyl)ethylglycine

N-(3-Mercapto-2-methylpropanoyl)-N-(3-tetrahydrothienyl)glycine

N-(3-Mercapto-2-methylpropanoyl)-N-(N-ethylpiperdine-3-yl)glycine

N-(2-Mercaptomethylbutanoyl)-N-2-(1-indol-3-yl-propyl)glycine

N-(3-Mercapto-2-methylpropanoyl)-N-2-methylenethienylglycine

N-(3-Mercapto-2-methylpropanoyl)-β-(2-thienyl)alanine

N-(3-Mercapto-2-methylpropanoyl)-β-(2-pyridyl)alanine

N-(3-Mercapto-2-methylpropanoyl)-N-(4-aminopyridyl)glycine

N-(3-Acetylthio-2-methylpropanoyl)-N-(1-isoquinolyl)glycine

N-(3-Acetylthio-2-methylpropanoyl)-N-(2-pyrimidyl)glycine

N-(3-Acetylthio-2-methylpropanoyl)-N-(2-benzimidazoyl)glycine

N-(3-Mercapto-2-methylpropanoyl)-N-(tetrahydrothiophene-1,1-dioxide 3-yl)glycine The compounds of the present invention have demonstrated potent activity (of the order $I_{50}$ of 0.017 to 0.030 micromols) in inhibiting the angiotensin converting enzyme (ACEI activity) when tested by the method described in Science 196, 441–4 (1977). As such, these compounds would be very useful in the treatment of hypertension.

The compounds of the present invention are somewhat structurally related to the compounds disclosed in German Offenlengunsschriften 2,717,548 and 2,753,824. However, the compounds disclosed in these publications possess an ACEI activity of about one three-hundredth shown by the compounds of the present invention.

Table I below lists the ACEI activity of representative compounds of the present invention. The $I_{50}$ value represents the amount in micromols required to give an inhibitive effect of 50% in the tests using the procedure described in the Science article.

TABLE I

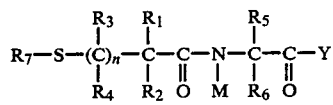

| M | $R_7$ | $I_{50}$ |
|---|---|---|
| Tetrahydrofurfyl | $CH_3CO$ | 1.4 |
| Furfuryl | $CH_3CO$ | 0.7 |
| Furfuryl | H | 0.16 |
| Tetrahydrofurfuryl | H | 0.13 |
| 1,1-Dioxytetrahydrothienyl | $CH_3CO$ | 2.2 |
| 1,1-Dioxytetrahydrothienyl | H | 0.2 |
| Thienylmethyl | $CH_3CO$ | 0.75 |
| N—Ethyl-2-pyrrolidylmethyl | H | 0.47 |
| Thienylmethyl | H | 0.055 |

The compounds of the present invention may be administered orally or parenterally in the treatment of hypertension, and it will be within the professional judgment and skill of the practitioner to determine the exact amount to be administered.

We claim:

1. Compounds of the structure:

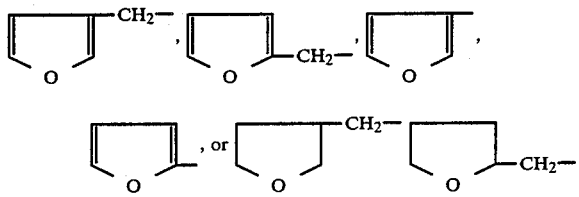

wherein
$R_1$, $R_2$, $R_3$, $R_4$, $R_5$ and $R_6$ are independently hydrogen, alkyl, alkenyl containing 2 to 6 carbon atoms, alkynyl containing 2 to 6 carbon atoms, phenylalkyl, or cycloalkyl containing 3 to 16 carbon atoms,
n is an integer from 0 to 4 inclusive,
M is heterocyclic or heterocyclic alkyl and is selected from the group consisting of

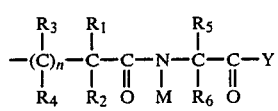

Y is hydroxy, alkoxy, amino, aminoalkanoyl, hydrocarbylaryloxy containing from 6 to 10 carbon atoms, aminoalkoxy, or hydroxyalkoxy, and
$R_7$ is hydrogen, alkanoyl, carboxylalkanoyl, hydroxyalkanoyl, amino-alkanoyl, cyano, amidino, carbalkoxy, ZS, or

wherein Z is hydrogen, alkyl, hydroxyalkyl, aminoalkyl or the radical

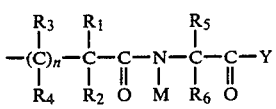

wherein $R_1$, $R_2$, $R_3$, $R_4$, $R_5$, $R_6$, n, M and Y are as described above; and where Y is hydroxy their nontoxic, pharmaceutically acceptable alkali metal, alkaline earth metal, and amine salts,
wherein the alkyl groups per se and alkyl moieties of groups containing an alkyl group, contain 1 to 6 carbon atoms.

2. A method of reducing the blood pressure in mammals having hypertension which comprises administering to said animals an effective amount of a compound according to claim 1.

3. Compounds of the structure

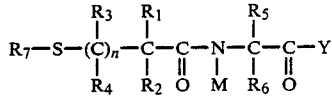

wherein
$R_1$, $R_2$, $R_3$, $R_4$, $R_5$ and $R_6$ are independently hydrogen, lower alkyl, lower alkenyl, lower alkynyl, phenyl-lower alkyl, or cycloalkyl, wherein the lower alkyl, lower alkenyl or lower alkynyl groups have up to 6 carbon atoms and the cycloalkyl groups have from 3 to 16 carbon atoms,
n is an integer from 0 to 4,
M is furyl, furfuryl, or tetrahydrofurfuryl,
Y is hydroxy, lower alkoxy having up to 6 carbon atoms, or amino,
$R_7$ is hydrogen, lower alkanoyl, benzoyl, ZS or

wherein the lower alkanoyl group contains up to 6 carbon atoms, and Z is hydrogen, lower alkyl containing up to 6 carbon atoms, or a radical of the formula

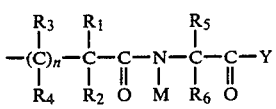

wherein $R_1$, $R_2$, $R_3$, $R_4$, $R_5$, $R_6$ and Y are as defined above, and where Y is hydroxy, their nontoxic pharmaceutically acceptable alkali metal, alkaline earth metal and amine salts.

4. A compound according to claim 3 wherein n is 1.

5. A compound according to claim 4 wherein Y is hydroxy.

6. A compound according to claim 5 wherein $R_1$, $R_3$, $R_4$, $R_5$ and $R_6$ are hydrogen and $R_2$ is lower alkyl.

7. A compound according to claim 6 wherein $R_2$ is methyl.

8. A compound according to claim 7 wherein $R_7$ is hydrogen.

9. A compound according to claim 7 wherein $R_7$ is alkanoyl.

10. A compound according to claim 7 wherein $R_7$ is acetyl.

11. A compound according to claim 7 wherein M is the group

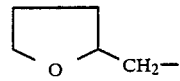

* * * * *